United States Patent
Doppalapudi et al.

(10) Patent No.: US 12,282,492 B2
(45) Date of Patent: Apr. 22, 2025

(54) INDICATING DIFFERENCES IN AND RECONCILING DATA STORED IN DISPARATE DATA STORAGE DEVICES

(71) Applicant: Bristol-Myers Squibb Company, Princeton, NJ (US)

(72) Inventors: Sahith Doppalapudi, Monroe Township, NJ (US); Sumit Nagpal, Iselin, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 158 days.

(21) Appl. No.: 17/849,189

(22) Filed: Jun. 24, 2022

(65) Prior Publication Data

US 2023/0048663 A1 Feb. 16, 2023

Related U.S. Application Data

(60) Provisional application No. 63/215,194, filed on Jun. 25, 2021, provisional application No. 63/215,210, filed on Jun. 25, 2021.

(51) Int. Cl.
*G06F 16/27* (2019.01)
*G06F 16/215* (2019.01)
*G06F 16/25* (2019.01)

(52) U.S. Cl.
CPC ............ *G06F 16/27* (2019.01); *G06F 16/215* (2019.01); *G06F 16/254* (2019.01)

(58) Field of Classification Search
CPC ....... G06F 16/27; G06F 16/215; G06F 16/254
(Continued)

(56) References Cited

U.S. PATENT DOCUMENTS

2014/0040182 A1* 2/2014 Gilder .................. G06F 16/256
707/602
2018/0060538 A1* 3/2018 Tiwari .................. G16H 10/60
(Continued)

OTHER PUBLICATIONS

Rouse, Margaret. "Composite Key". Techopedia. Published Jun. 15, 2017. Accessed May 4, 2024 from <https://www.techopedia.com/definition/6572/composite-key> (Year: 2017).*

*Primary Examiner* — Robert W Beausoliel, Jr.
*Assistant Examiner* — Lauren Zannah Ganger
(74) *Attorney, Agent, or Firm* — Honigman LLP; Grant Griffith; Jonathan P. O'Brien

(57) ABSTRACT

Provided herein are system, apparatus, device, method and/or computer program product embodiments, and/or combinations and sub-combinations thereof, for generating an output indicating differences in the data stored in disparate data storage devices and/or for reconciling data stored in disparate data storage devices. In an embodiment, a server loads a first subset of a first set of data corresponding to one or more first columns and a second subset of a second set of data corresponding to one or more second columns into a data repository. The server identifies one or more differences between the first subset of data and the second subset of data in the data repository, and causes display of the one or more differences. The server may generate an output including the first and second sets of data, and a visual indicator indicating each of the one or more differences and causes display of the output.

24 Claims, 7 Drawing Sheets

(58) Field of Classification Search
USPC .......................................................... 707/610
See application file for complete search history.

(56) References Cited

U.S. PATENT DOCUMENTS

| | | | |
|---|---|---|---|
| 2018/0129374 A1* | 5/2018 | Kim | G06F 3/0482 |
| 2019/0034475 A1* | 1/2019 | Parikh | G06F 16/2365 |
| 2020/0279623 A1* | 9/2020 | Ozeran | G06F 16/215 |

* cited by examiner

Help

Safety Gateway Reconciliation Report

Protocol Number: 1234

Product Name

Total # of Cases in Safety DB    12    Total # of Cases in Clinical DB    46
Total # of Events in Safety DB   25    Total # of Events in Clinical DB   68

1. This report is reconciling data between clinical database and the safety database.
2. This report is identifying the following discrepancies.

- If case is not present in clinical database.
   - If case is not present in Safety database.
   - If there is a mismatch in the following attributes.

Event/Case Attribute Mismatch which refers to the mismatches in any of the below.
   - Seriousness
   - AE Stop Date
   - Outcome
   - Age
   - Gender Casualty Mismatch – refers to the mismatch in the Casualty
Preferred Term Mismatch – refers to the mismatch in the Preferred Term

| | | | | | | | | | | | | | | ↓ 401 |
|---|---|---|---|---|---|---|---|---|---|---|---|---|---|---|
| Missing in Clinical DB | Missing in Safety DB | Event/Case Attribute Mismatch | | Causality Mismatch | | Accurate Data | | | | | | | | |

↓420

| Source | Site # | Subject ID | AER Number | Case ID | Reported Term | Seriousness | Co-Manifestation | Preferred Term | AE Onset Date | AE Stop Date | Outcome | Age | Gender | Product | Causality | Mismatch |
|---|---|---|---|---|---|---|---|---|---|---|---|---|---|---|---|---|
| Clinical Data | 123 | 123456 | AER 123 | Case 123 | NAUSEA | Yes | N | 1211 (Nausea) | 18/DEC/2020 | 25/DEC/2020 | Recovered/Resolved | XX | MALE | Product A | NOT SUSPECTED | Yes |
| Safety Data | 123 | 123456 | AER 123 | Case 123 | NAUSEA | No | N | 1211 (Nausea) | 18/DEC/2020 | 25/DEC/2020 | Recovered/Resolved | XX | MALE | Product A | | Yes |
| Clinical Data | 123 | 123456 | AER 123 | Case 123 | NAUSEA | Yes | N | 1211 | 18/DEC/2020 | 25/DEC/2020 | RECOVERED/RESOLVED | XX | MALE | Product B | NOT SUSPECTED | Yes |
| Safety Data | 123 | 123456 | AER 123 | Case 123 | NAUSEA | No | N | 1211 (Nausea) | 18/DEC/2020 | 25/DEC/2020 | Recovered/Resolved | XX | MALE | Product B | | Yes |
| Clinical Data | 456 | 123456 | | Case 123 | NAUSEA | Yes | N | 1211 | 17/AUG/2019 | 20/AUG/2019 | RECOVERED/RESOLVED | | MALE | Product A | NOT SUSPECTED | Yes |
| Safety Data | 456 | 123456 | | | | | | () | | | | | | | | |
| | | | | | | | | | | | | | | | | |
| Safety Data | 789 | 789456 | AER 456 | Case 123 | HEADACHE | Yes | N | 1456 (Headache) | 01/MAR/2018 | 10/MAR/2018 | Recovered/Resolved | | | Product A | | Yes |
| Safety Data | 789 | 789456 | AER 456 | Case 123 | HEADACHE | Yes | N | 1456 | 01/JUL/2019 | 10/JUL/2019 | Recovered/Resolved | | | Product B | | Yes |
| Clinical Data | 789 | 789456 | | | HEADACHE | Yes | N | 1456 | | 10/JUL/2019 | RECOVERED/RESOLVED | | | Product A | | Yes |
| Safety Data | 789 | 789456 | | Case 123 | HEADACHE | Yes | N | 1456 | | 10/MAR/2019 | RECOVERED/RESOLVED | | | Product B | | Yes |
| Clinical Data | 789 | 789456 | | | | | | () | | | | | | | | |
| Clinical Data | 147 | 123258 | AER 789 | Case 123 | NAUSEA | Yes | N | 1211 | 12/JUN/2019 | | Recovered | XX | FEMALE | Product C | SUSPECTED | Yes |
| Safety Data | 147 | 123258 | AER 789 | Case 123 | NAUSEA | Yes | N | 1211 (Nausea) | 12/JUN/2019 | | | XX | FEMALE | Product C | | Yes |
| Clinical Data | 147 | 123258 | AER 789 | Case 123 | NAUSEA | Yes | N | 1211 | 12/JUN/2019 | | | XX | FEMALE | Product A | NOT SUSPECTED | Yes |

INDICATING DIFFERENCES IN AND RECONCILING DATA STORED IN DISPARATE DATA STORAGE DEVICES

CROSS-REFERENCE TO RELATED APPLICATIONS

The present application claims the benefit of U.S. Provisional Patent Application No. 63/215,194, filed Jun. 25, 2021 and U.S. Provisional Patent Application No. 63/215,210, filed Jun. 25, 2021, each of which is incorporated herein by reference in its entirety.

BACKGROUND

Entities, such as companies, government institutions, educational institutions, or the like, store common data in two or more data storage devices. However, there can be differences or omissions of data in one or more data storage devices. As a result, the entities may need to reconcile the data to identify the differences in the data between one or more data storage devices. However, conventional systems require individually inspecting numerous files to identify the differences. This can be error-prone and operationally expensive.

SUMMARY

Provided herein are system, apparatus, device, method, and/or computer program product embodiments, and/or combinations and sub-combinations thereof, for generating an output indicating differences in data stored in disparate data storage devices.

Further provided herein are system, apparatus, device, method, and/or computer program product embodiments, and/or combinations and sub-combinations thereof, for reconciling data stored in disparate data storage devices.

A given embodiment includes a computer-implemented method for generating an output indicating differences in data stored in disparate data storage devices. The method includes loading a first set of data corresponding to one or more first columns of a first database and a second set of data corresponding to a one or more second columns of a second database into a data repository. The first set of data comprises one or more first rows and the second set of data comprises one or more second rows and the data repository includes a set of columns corresponding to the first and second sets of data. The method further includes identifying one or more differences between the first set of data and the second set of data in the data repository. Additionally, the method includes generating an output including the first set of data and the second set of data, and a visual indicator indicating each of the one or more differences, and causing display of the output.

Another embodiment includes a system for generating an output indicating differences in data stored in disparate data storage devices. The system includes a memory and a processor coupled to the memory. The processor is configured to load a first set of data corresponding to one or more first columns of a first database and a second set of data corresponding to a one or more second columns of a second database into a data repository. The first set of data comprises one or more first rows and the second set of data comprises one or more second rows and the data repository includes a set of columns corresponding to the first and second sets of data. The processor is further configured to identify one or more differences between the first set of data and the second set of data in the data repository. Additionally, the processor is configured to generate an output including the first set of data and the second set of data, and a visual indicator indicating each of the one or more differences, and cause display of the output.

A further embodiment includes a non-transitory computer-readable medium having instructions stored thereon, execution of which, by one or more processors of a device, cause the one or more processors to perform operations. The operations include loading a first set of data corresponding to one or more first columns of a first database and a second set of data corresponding to a one or more second columns of a second database into a data repository. The first set of data comprises one or more first rows and the second set of data comprises one or more second rows and the data repository includes a set of columns corresponding to the first and second sets of data. The operations further include identifying one or more differences between the first set of data and the second set of data in the data repository. Additionally, the operations include generating an output including the first set of data and the second set of data, and a visual indicator indicating each of the one or more differences, and causing display of the output.

Another embodiment includes a computer-implemented method for generating an output indicating differences in data stored in disparate data storage devices. The method includes loading a first set of data corresponding to one or more first columns of a clinical database and a second set of data corresponding to a one or more second columns of a safety database into a data repository. The first set of data comprises one or more first rows and the second set of data comprises one or more second rows and the data repository includes a set of columns corresponding to the first and second sets of data. The method further includes identifying one or more differences between the first set of data and the second set of data in the data repository. Additionally, the method includes generating an output including the first set of data and the second set of data, and a visual indicator indicating each of the one or more differences, and causing display of the output.

Another embodiment includes a system for generating an output indicating differences in data stored in disparate data storage devices. The system includes a memory and a processor coupled to the memory. The processor is configured to load a first set of data corresponding to one or more first columns of a clinical database and a second set of data corresponding to a one or more second columns of a safety database into a data repository. The first set of data comprises one or more first rows and the second set of data comprises one or more second rows and the data repository includes a set of columns corresponding to the first and second sets of data. The processor is further configured to identify one or more differences between the first set of data and the second set of data in the data repository. Additionally, the processor is configured to generate an output including the first set of data and the second set of data, and a visual indicator indicating each of the one or more differences, and cause display of the output.

A further embodiment includes a non-transitory computer-readable medium having instructions stored thereon, execution of which, by one or more processors of a device, cause the one or more processors to perform operations. The operations include loading a first set of data corresponding to one or more first columns of a clinical database and a second set of data corresponding to a one or more second columns of a safety database into a data repository. The first set of data comprises one or more first rows and the second set of data comprises one or more second rows and the data repository includes a set of columns corresponding to the first and second sets of data. The operations further include identifying one or more differences between the first set of data and the second set of data in the data repository. Additionally, the operations include generating an output including the first set of data and the second set of data, and a visual indicator indicating each of the one or more differences, and causing display of the output.

Another embodiment includes a computer-implemented method for reconciling data stored in disparate storage devices. The method includes retrieving one or more first data files including a first set of data stored in a first database. Furthermore, the method includes retrieving one or more second data files including a second set of data stored in a second database. The method further includes identifying one or more first columns in the one or more first data files and one or more second columns in the one or more second data files. Additionally, the method includes loading a first subset of the first set of data and a second subset of the second set of data into a data repository. The first subset of data corresponds to the one or more first columns and comprises one or more first rows, and the second subset of data corresponds to the one or more second columns and comprises one or more second rows. The data repository includes a set of columns corresponding to the first and second subsets of data. Furthermore, the method includes identifying one or more differences between the first subset of data and the second subset of data in the data repository and causes display of the one or more differences.

Another embodiment includes a system for reconciling data stored in disparate storage devices. The system includes a memory and a processor coupled to the memory. The processor is configured to retrieve one or more first data files including a first set of data stored in a first database. The processor is further configured to retrieve one or more second data files including a second set of data stored in a second database. Furthermore, the processor is configured to identify one or more first columns in the one or more first data files and one or more second columns in the one or more second data files. Additionally, the processor is configured to load a first subset of the first set of data and a second subset of the second set of data into a data repository. The first subset of data corresponds to the one or more first columns and comprises one or more first rows, and the second subset of data corresponds to the one or more second columns and comprises one or more second rows. The data repository includes a set of columns corresponding to the first and second subsets of data. Furthermore, the processor is configured to identifying one or more differences between the first subset of data and the second subset of data in the data repository and causes display of the one or more differences.

A further embodiment includes a non-transitory computer-readable medium having instructions stored thereon, execution of which, by one or more processors of a device, cause the one or more processors to perform operations. The operations include retrieving one or more first data files including a first set of data stored in a first database. Furthermore, the operations include retrieving one or more second data files including a second set of data stored in a second database. The operations further include identifying one or more first columns in the one or more first data files and one or more second columns in the one or more second data files. Additionally, the operations include loading a first subset of the first set of data and a second subset of the second set of data into a data repository. The first subset of data corresponds to the one or more first columns and comprises one or more first rows, and the second subset of data corresponds to the one or more second columns and comprises one or more second rows. The data repository includes a set of columns corresponding to the first and second subsets of data. Furthermore, the operations include identifying one or more differences between the first subset of data and the second subset of data in the data repository and causes display of the one or more differences.

Another embodiment includes a method for reconciling data stored in disparate storage devices. The method includes retrieving one or more first data files including a first set of data stored in a clinical database, and retrieving one or more second data files including a second set of data stored in a safety database. The method further includes identifying one or more first columns in the one or more first data files and one or more second columns in the one or more second data files. Additionally, the method includes loading a first subset of the first set of data and a second subset of the second set of data into a data repository. The first subset of data corresponds to the one or more first columns and comprises one or more first rows, and the second subset of data corresponds to the one or more second columns and comprises one or more second rows. The data repository includes a set of columns corresponding to the first and second subsets of data. Furthermore, the method includes identifying one or more differences between the first subset of data and the second subset of data in the data repository and causing display of the one or more differences.

A further embodiment includes a system for reconciling data stored in disparate storage devices. The system includes a memory and a processor coupled to the memory. The processor is configured to retrieve one or more first data files including a first set of data stored in a clinical database, and retrieve one or more second data files including a second set of data stored in a safety database. The processor is further configured to identify one or more first columns in the one or more first data files and one or more second columns in the one or more second data files. Additionally, the processor is configured to loading a first subset of the first set of data and a second subset of the second set of data into a data repository. The first subset of data corresponds to the one or more first columns and comprises one or more first rows, and the second subset of data corresponds to the one or more second columns and comprises one or more second rows. The data repository includes a set of columns corresponding to the first and second subsets of data. Furthermore, the processor is configured to identify one or more differences between the first subset of data and the second subset of data in the data repository, and causing display of the one or more differences.

A further embodiment includes a non-transitory computer-readable medium having instructions stored thereon, execution of which, by one or more processors of a device, cause the one or more processors to perform operations. The operations include retrieving one or more first data files including a first set of data stored in a clinical database, and retrieving one or more second data files including a second set of data stored in a safety database. The operations further include identifying one or more first columns in the one or more first data files and one or more second columns in the one or more second data files. Additionally, the operations include loading a first subset of the first set of data and a second subset of the second set of data into a data repository. The first subset of data corresponds to the one or more first columns and comprises one or more first rows, and the second subset of data corresponds to the one or more second columns and comprises one or more second rows. The data repository includes a set of columns corresponding to the first and second subsets of data. Furthermore, the operations include identifying one or more differences between the first subset of data and the second subset of data in the data repository and causing display of the one or more differences.

BRIEF DESCRIPTION OF THE FIGURES

The accompanying drawings, which are incorporated herein and form part of the specification, illustrate the present disclosure and, together with the description, further serve to explain the principles of the disclosure and enable a person skilled in the relevant art to make and use the disclosure.

FIG. 3 is a graphical user interface part of an output generated by the system for reconciling data stored in disparate data storage devices, according to some embodiments.

FIG. 4 is a graphical user interface part of an output generated by the system for reconciling data stored in disparate data storage devices, according to some embodiments.

The drawing in which an element first appears is typically indicated by the leftmost digit or digits in the corresponding reference number. In the drawings, like reference numbers may indicate identical or functionally similar elements.

DETAILED DESCRIPTION

Figure 1:
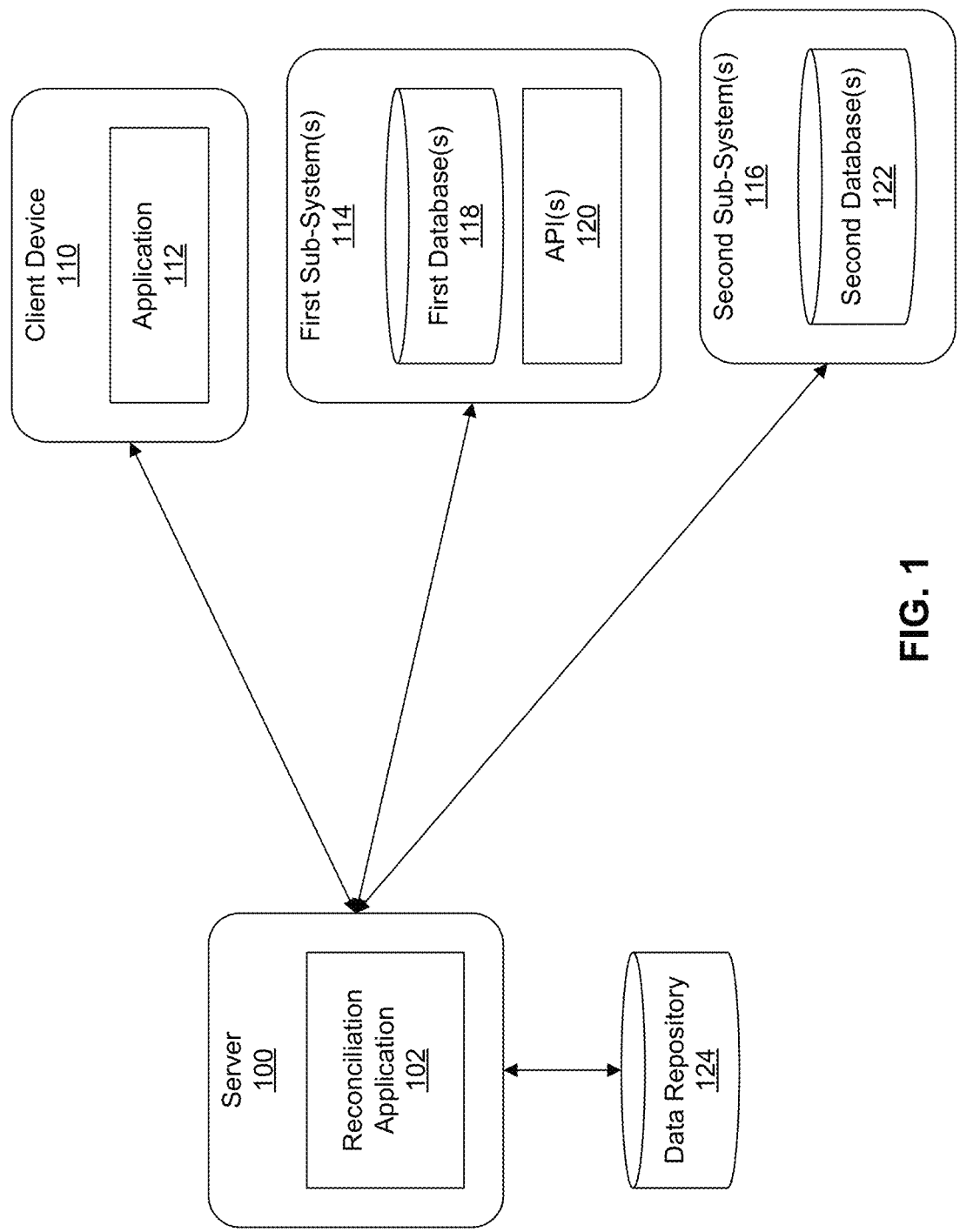
FIG. 1 is a block diagram of an example system for reconciling data stored in disparate data storage devices.

Provided herein are system, apparatus, device, method, and/or computer program product embodiments, and/or combinations and sub-combinations thereof, for generating an output indicating differences in data stored in disparate data storage devices.

Further provided herein are system, apparatus, device, method, and/or computer program product embodiments, and/or combinations and sub-combinations thereof, for reconciling data stored in disparate data storage devices.

As described above, conventional methods for reconciling data stored in disparate data storage devices may be burdensome, costly, and error-prone. For example, in the field of pharmacovigilance (PV) operations, a first database may store clinical trial data, and a second database may store drug safety data. The first and second databases may include similar columns storing data regarding a particular drug or product. Therefore, the first and second databases should share the same data associated with the particular drug or product. However, frequently, there is a mismatch or missing data in either the first or second database. As a result, the data needs to be reconciled so the difference in the data may be resolved.

Conventional systems require manual review of spreadsheets, including the data stored in the first and second databases. In one example, each clinical trial may include 24 spreadsheets of data. Reconciling the 24 spreadsheets of data per study per year with the data stored in the safety database may require 200 hours/year and cost over $25,000/year. As a result, conventional systems may be operationally expensive and error-prone.

Embodiments described herein solve the technical challenges posed by conventional systems by automatically reconciling data stored in data storage devices and indicating the differences between the two data storage devices. In some embodiments, the differences between the two data storage devices is indicated visually. In some embodiments, a server retrieves one or more first data files including a first set of data stored in a first database. The server retrieves one or more second data files including a second set of data stored in a second database. Furthermore, the server identifies one or more first columns in the one or more first data files and one or more second columns in the one or more second data files. The server loads a first subset of the first set of data corresponding to the one or more first columns and a second subset of the second set of data corresponding to the one or more second columns into a data repository. The first subset of data comprises one or more first rows, and the second subset of data comprises one or more second rows, and the data repository includes a set of columns corresponding to the first and second subsets of data. Additionally, the server identifies one or more differences between the first subset of data and the second subset of data in the data repository and causes display of the one or more differences.

In some embodiments, the server loads a first set of data corresponding to one or more first columns of a first database and a second set of data corresponding to one or more second columns of a second database into a data repository. The first set of data comprises one or more first rows. The second set of data comprises one or more second rows. The data repository includes a set of columns corresponding to the first and second sets of data. Furthermore, the server identifies one or more differences between the first set of data and the second set of data in the data repository. The server generates an output including the first set of data and the second set of data, and a visual indicator indicating each of the one or more differences and causes display of the output.

Embodiments described herein provide for automatically identifying differences between different data storage devices. This eliminated the generation of about 1,320 spreadsheets involved in the reconciliation process. Furthermore, the output visually indicates the differences between the data in the different data storage devices. This allows for quickly correcting the data stored in a respective data storage device. As a result, embodiments described herein eliminate the extensive hours, manpower, and potential errors caused by conventional systems when reconciling data.

FIG. 1 is a block diagram of a system for reconciling data stored in disparate data storage devices. The system may include a server 100, client device 110, first sub-system(s) 114, second sub-system(s) 116, and data repository 124. The devices of the system may be connected through a network. For example, the devices of the system may be connected through wired connections, wireless connections, or a combination of wired and wireless connections. In an example embodiment, one or more portions of the network may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

Client device 110 includes application 112. Application 112 may be configured to transmit requests for reconciling data to server 100. For example, in response to client device 110 launching application 112, a user may input their user credentials. Application 112 may authenticate the user based on their user credentials. As a non-limiting example, users may log in to application 112 using a Windows Active Directory login. In response to authenticating the user, application 112 may allow the user to provide input associated with requests for reconciling data stored in different data storage devices. The request may include identifiers for the data storage devices. The request may also include a time period of data to be reconciled. For example, the request may include instructions for reconciling data added to the respective data storage devices in the last six months.

Server 100 may include reconciliation application 102. Reconciliation application 102 may be configured to reconcile data stored in disparate data storage devices in response to receiving a request from application 112. This may involve executing Extract Transform Load (ETL) operations with respect to data storage devices, such as loading data, extracting data, transforming data, deleting data, transferring data, etc. Reconciliation application 102 may also be configured to generate an output identifying differences between data stored in disparate data storage devise. In some embodiments, reconciliation application 102 may be configured to periodically reconcile the data stored in disparate data storage devices without being prompted by application 112.

First sub-system 114 may be a third-party system configured to store first database(s) 118. First database 118 may be a data storage device configured to store structured or unstructured data. First sub-system 114 may store multiple first databases 118. Each of the databases stored in first sub-system 114 may store a different type of data. Furthermore, first sub-system 114 may include Application Program Interface(s) (APIs) 120.

Reconciliation application 102 may access the data stored in first database 118 using API 120. Each API 120 may provide access to a particular type of data. As a result, a particular API may be used to access data stored in first database 118. API 120 may expose the data stored in first database 118 to reconciliation application 102 in the form of a file, such as a spreadsheet (e.g., a MICROSOFT EXCEL file).

Second sub-system 116 may be configured to store second database(s) 122. Second database 122 may be a data storage device configured to store structured or unstructured data. Reconciliation application 102 may be configured to access the data stored in second database 122 to reconcile the data stored in first database 118 and second database 122.

Data repository 124 may be a data storage device configured to store data extracted from first database 118 and second database 122. Data repository 124 may include a subset of the columns of first database 118 and second database 122.

Figure 2:
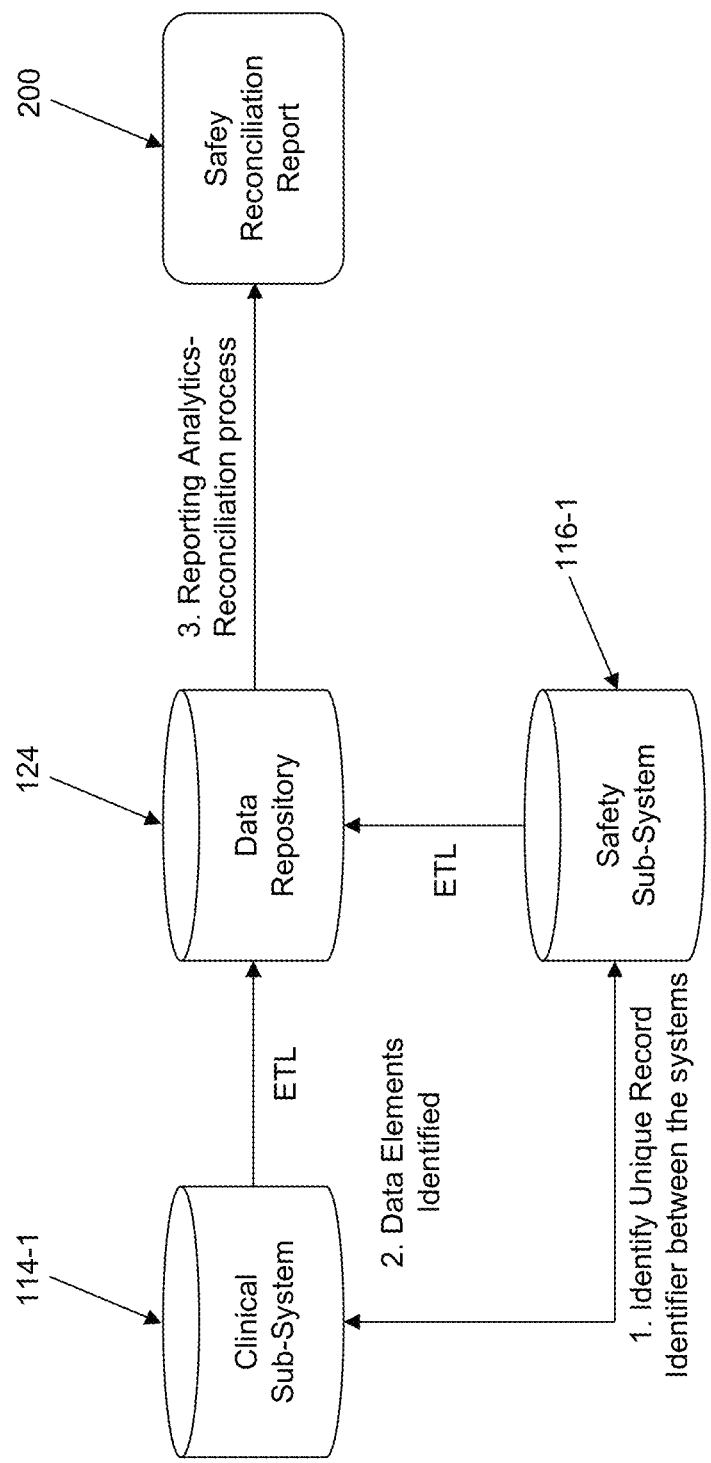
FIG. 2 is a block diagram of a system for reconciling clinical and safety data, according to some embodiments.

FIG. 2 is a block diagram of a system for reconciling clinical and safety data, according to some embodiments. FIG. 2 will be described with respect to FIG. 1. As a non-limiting example, first sub-system 114 may be a clinical sub-system 114-1, and second sub-system 116 may be safety sub-system 116-1.

Clinical sub-system 114-1 may include first database 118. First database 118 may be a clinical database. Specifically, first database 118 may store data associated with clinical trials of one or more drugs or products. For example, the data may include the timeline of the clinical trial, drug or product included in the clinical trial, information about the subject (e.g., user), the effect of the drug or product, etc. First database 118 may store data associated with a single clinical trial. Alternatively, first database 118 may store data associated with multiple clinical trials. Furthermore, clinical sub-system 114-1 may be associated with an entity responsible for conducting the clinical trials. As such, the entity may be conducting numerous different clinical trials. Therefore, clinical sub-system 114-1 may store multiple first databases 118. Each first database 118 may be associated with a single clinical trial. Each clinical trial may be referred to as a protocol.

Safety sub-system 116-1 may include second database 122. Second database 122 may be a safety database. Second database 122 may store safety data associated with drugs or other products. For example, second database 122 may store data related to pharmacovigilance (PV). The data may include information about a drug or product, information about a subject (e.g., user), and information about a reported adverse effect to using the drug or product. Second database 122 may store data associated with a single drug or product (e.g., safety reports regarding a particular drug or product). Alternatively, second database 122 may store data associated with multiple different drugs or products.

First database 118 and second database 120 may store information associated with adverse effects experienced by subjects and caused by products or drugs. For example, an adverse event is a serious adverse event if it satisfies one of the following requirements: results in death or is life-threatening, requires inpatient hospitalization or extends an existing hospitalization; results in persistent or significant disability or incapacity; results in a congenital disability; or is otherwise medically significant because treatment and/or intervention is required to prevent one of the preceding requirements. Furthermore, when performing clinical trials of drugs or other products, it may be determined whether an adverse effect is a serious unexpected result adverse reaction (SUSAR).

First database 118 may share common data associated with patients, drugs, and products. Moreover, first database 118 a first set of columns, and second database 122 may include a second set of columns. The first set of columns and second set of columns may include one or more similar columns. To that end, the data associated with the same drug, product, and/or patient for the one or more similar columns should be the same across first database 118 and second database 122. For example, both first database 118 and second database 122 may include data associated with site number, subject ID, AER number, case identifier, reported term, seriousness, co-manifestation, preferred term, adverse effect onset date, adverse effect stop date, outcome, age, gender, product, and causality. The data corresponding to these columns and associated with the same drug, product, and/or patient should be the same in first database 118 and second database 122.

As a non-limiting example, data repository 124 may include a site number column, subject ID column, AER number column, case identifier column, reported term column, seriousness column, co-manifestation column, preferred term column, adverse effect onset date column, adverse effect stop date column, outcome column, age column, gender column, product column, and causality column.

The site number column may include data values indicating an identifier of the site of a clinical trial. The subject ID column may include data values indicating an identifier of the subject part of the clinical trial or a subject reporting an adverse effect. The AER number column may include data values indicating adverse effect report (AER) number. The case ID column may include data values indicating an identifier for a case for a reported adverse effect. The reported term column may include data values corresponding to a reported event (e.g., headache, nausea, fever, etc.). The reported event may be an adverse effect. The seriousness column may include data values that indicate whether the adverse effect is serious. The preferred term column may include data values that indicate an identifier and preferred description of the reported event. The adverse effect onset date column may store data values that indicate a date that the adverse effect began. The adverse effect stop date column may store data values that indicate a date the adverse effect ended. The outcome column may store data values that indicate an outcome of the reaction or adverse event (resolved or recovered). The age column may store data values indicating the age of the subject. The gender column may store data values that indicate the gender of the subject. The product column may include data values that indicate an identifier of the product (for the clinical trial or which may have caused the adverse effect). The casualty column may include data values that indicate whether the product caused the adverse effect.

However, differences may exist between first database 118 and second database 122. For example, the first database 118 may be updated while second database 122 is not updated, or vice versa. Additionally, there may be an incorrect update/addition/deletion of data in either first database 118 or second database 122. As a result, there may be a mismatch of data between first database 118 and second database 122. Furthermore, there may missing data in either first database 118 or second database 122. The missing data may include a single missing entry or a missing row.

In some embodiments, reconciliation application 102 may receive a request to reconcile the data in first database 118 and second database 122 from application 112. The request may include an identifier of clinical sub-system 114-1, first database 118, safety sub-system 116-1, and/or second database 122. Alternatively, or in addition to, the request may include an identifier for a particular clinical trial (e.g., protocol ID), drug, or product. The request may also include a time period. Specifically, the request may include instructions to reconcile data for data that has been loaded in first database 118 and second database 122 over a given time period.

Reconciliation application 102 may identify first database 118 and second database 122 using the identifier of clinical sub-system 114-1, first database 118, safety sub-system 116-1, and/or second database 122. Alternatively, or in addition to, reconciliation application 102 may identify first database 118 and second database 122 based on the identifier for a particular clinical trial (e.g., protocol ID), drug, or product.

Reconciliation application 102 may interface with API 120 to access the data of first database 118. API 120 may expose one or more data files to reconciliation application 102. For example, API 120 may expose the data of first database 118 in the form of a file, such as a spreadsheet. The spreadsheet may include the first set of columns of first database 118. As a non-limiting example, the first set of columns may include project ID, project, internal ID for the study, environment, internal ID for the subject, internal ID for the study site, subject name or identifier, SDVTier, internal ID for the site, site name, site number, site group, internal id for the instance, folder instance name, instance repeat number, internal id for the folder, folder OID, folder name, folder sequence number, total days from study start, internal ID for data page, eCRF page name, sequence number for eCRF page in folder, clinical date of record, internal ID for the record, earliest data creation, timestamp of last save in clinical view, last data update time, coder hierarchy, SE site number, study environment site number, age, age character, sex, sex code, ethnicity, ethnicity code, race, race code, age unit, age unit code, enrollment date, enrollment date character, birth year, birth year character, age at onset of SAE for SG, related adverse effect record, related adverse effect code, reported term for adverse effect, start date of adverse effect, seriousness, end date of adverse effect, etc.

Reconciliation application 102 may identify one or more columns of the first set of columns corresponding to data to be loaded into data repository 124. The data to be loaded into data repository 124 may correspond with the one or more columns of data repository 124. For example, reconciliation application 102 may identify one more columns in the one or more data files that store data associated with the site number, subject ID, AER number, case identifier, reported term, seriousness, co-manifestation, preferred term, adverse effect onset date, adverse effect stop date, outcome, age, gender, product, and causality.

Reconciliation application 102 may execute an ETL operation to extract the data corresponding to the data from the one or more columns in the first set of columns. Furthermore, reconciliation application 102 may execute an ETL operation to transform the extracted data such that it can be loaded into data repository 124. Reconciliation application 102 may map the extracted data to the one or more columns of data repository 124. Each of the columns may be configured to receive data in a particular format. Elements of the extracted data may need to be combined and transformed to be loaded into a respective column. Transform operations may include cleaning, deduplication, format revision, key restructuring, derivation, filtering, joining, splitting, data validation, summarization, aggregation, integration, etc. For example, reconciliation application 102 may implement the following transformation and mapping rules:

| Line Listing attribute for reconciliation | RaveEDC clinical view: Form OID > Field OID | SDM: Table > Column | Transformation/mapping Rules |
| --- | --- | --- | --- |
| N/A | DM* > Project AE* > Project | STG_SAFETY_RECON_ VELOCITY > PROTOCOL_NO_ | Inner join criteria among SAE Relevant Study Treatment, IE*, DM* & AE* forms |

-continued

| Line Listing attribute for reconciliation | RaveEDC clinical view: Form OID > Field OID | SDM: Table > Column | Transformation/mapping Rules |
|---|---|---|---|
| Center # | DM* > Subject AE* > Subject | STG_SAFETY_RECON_VELOCITY > SITE_NO_ | Inner join criteria among SAE Relevant Study Treatment, IE*, DM* & AE* Forms Center# is 3-digit value which is first 3 digits of AE* > Subject excluding last 4 digits. Append 0's as prefix to form 3-digit value |
| Study Patient # | DM* > Subject AE* > Subject | STG_SAFETY_RECON_VELOCITY > STUDY_PATIENT_NO | Inner join criteria among SAE Relevant Study Treatment, IE*, DM* & AE* Forms Study Patient# is 4-digit value which is last 4 digits of AE* > Subject |
| N/A | AE* > X_CASEIDDSL | STG_SAFETY_RECON_VELOCITY > RAVE_CASE_NO | For null cases, populate the case number in below format BLANK_CASE_' \|\| AE* > Project \|\| '_' \|\| AE* > Subject |
| Reported (Verbatim) Term | AE* > DX_AETERM | STG_SAFETY_RECON_VELOCITY > EVENT_REPORTED_TERM | N/A |
| MedDRA Preferred (Coded) Term | AE* > DX_PT | STG_SAFETY_RECON_VELOCITY > EVENT_PT | N/A |
| Reporter Seriousness | AE* > AESER | STG_SAFETY_RECON_VELOCITY > REPORTER_SERIOUSNESS | Only include the worst AESER for each distinct X_CASEIDDSL, DX_AETERM, and DX_PT. The worst AESER is defined as: 1. (worst): 'Yes' 2. 'No' 3. Null |

| Line Listing attribute for reconciliation | RaveEDC clinical view: Form OID > Field OID | SDM: Table > Column | Transformation/mapping Rules |
|---|---|---|---|
| Reporter Outcome | AE* > AEOUT | STG_SAFETY_RECON_VELOCITY > REPORTER_OUTCOME | Only include the latest AEOUT for each distinct X_CASEIDDSL, DX_AETERM, DX_PT and DV_AESAESTDAT. The latest AEOUT is defined as the AE* record having the maximum RECORDID when grouped by X_CASEIDDSL, DX_AETERM, DX_PT and DV_AESAESTDAT. |
| Age | DM* > DX_AEONSET | STG_SAFETY_RECON_VELOCITY > PATIENT_AGE_IN_YEARS | N/A |
| Gender | DM* > M_SEX | STG_SAFETY_RECON_VELOCITY > PATIENT GENDER | N/A |
| AE Onset Date | AE* > DV_AESAESTDAT | STG_SAFETY_RECON_VELOCITY > AE ONSET DATE | For null Rave cases, AE Onset Date should be on or after the Therapy Start Date. Please refer Section 3.16 for details. |

| Line Listing attribute for | RaveEDC clinical view: Form OID > | SDM: Table > Column | Transformation/mapping Rules |
|---|---|---|---|
| AE Stop Date | AE* > DV_AESAEENDAT | STG_SAFETY_RECON_VELOCITY > AE_STOP_DATE_ | Only include the latest DV_AESAEENDAT for each distinct X_CASEIDDSL, DV_AESAESTDAT. The |

-continued

| Line Listing attribute for | RaveEDC clinical view: Form OID > | SDM: Table > Column | Transformation/mapping Rules |
|---|---|---|---|
| Eligible? | IE* > X_IEYN | STG_SAFETY_RECON_VELOCITY > IS_ELIGIBLE | latest DV_AESAEENDAT is defined as the AE* record having the maximum RECORDID when grouped by X_CASEIDDSL, DX_AETERM, DX_PT and DV_AESAESTDAT. Inner join criteria between IE* & AE* forms on projectid, siteid and subjectid |

| Line Listing attribute for reconciliation | RaveEDC clinical view: Form OID > Field OID | SDM: Table > Column | Transformation/mapping Rules |
|---|---|---|---|
| Relationship to Study Treatment | AE_SAE_U01 > AEREL_XXX | STG_SAFETY_RECON_CAUSALITY > REL_TO_STUDY_TREATMENT | Get AEREL_XXX (Causality) for each distinct X_CASEIDDSL, DX_AETERM, and DX_PT provided AE* > X_RELTRT_XXX (Product) exists in Study Treatment (X_ECTRT) on the SAE Relevant Study Treatment form. The XXX is replaced with 3-character code for study treatment. List of products for a given study can vary from 1 to 10 (max). ETL must transpose column level AE_REL_XXX values to multiple rows. There is one AEREL_XXX variable per study treatment in the study, even if the patient is not taking the drug. If there is no corresponding Study Treatment (X_ECTRT) on the SAE Relevant Study Treatment form (XX_ECSAEREL), the variable should be dropped from the reconciliation. |
| Study Treatment | XX_ECSAEREL > X_ECTRT | STG_SAFETY_RECON_CAUSALITY > STUDY_TREATMENT | Inner join between SAE Relevant Study Treatment and AE* forms on projected, siteid and subjectid. The first doses of all study treatments entered on the Study Drug Exposure forms are mapped to SAE Relevant Study Treatment form (XX_ECSAEREL). This form shows only those study drugs taken by the subject at the time of the event. |

Please note the following acronyms and definitions for the above transformations and mappings:

| Term | Definition |
|---|---|
| AE | Adverse Event/Serious Adverse Event forms including the entire universe of AE forms |
| CBD | Clinical Database |
| CRF | Case Report Form or eCRF |
| CSV | Comma-separated values |
| DM | Demographics forms, including the entire universe of DM forms |
| EDC | Electronic Data Capture |

-continued

| Term | Definition |
| --- | --- |
| OID | Object Identifier for CRF |
| ODI | Oracle Data Integrator (extract, load, transform middleware application) |
| PII/PHI | Personally Identifiable Information/Private Health Information |
| RWS | Rave Web Services |
| SDB | Safety Database |
| SDM | System Design Specification |
| SDS | System Design Specification |
| SGR | Safety Gateway Reconciliation |
| IE | Eligibility forms, including the entire universe of IE forms |
| XX_ECSAEREL | SAE Relevant Study Treatment form |

Reconciliation application 102 may detect imprecise or partial dates. Furthermore, reconciliation application 102 may transform the missing days and months in the imprecise or partial dates to 01 and JAN, respectively.

Reconciliation application 102 may execute an ETL operation to load the transformed data into data repository 124. The transformed data may be loaded into the respective columns in data repository 124.

Reconciliation application 102 may interface with safety sub-system 116-1 to extract data from second database 122. In some embodiments, reconciliation application 102 may retrieve one or more data files that include a copy of the data stored in second database 122. The one or more data files may include a second set of columns.

Reconciliation application 102 may identify one or more columns of the second set of columns corresponding to data to be loaded into data repository 124. For example, reconciliation application 102 may identify one more columns that store data associated with the site number, subject ID, AER number, case identifier, reported term, seriousness, co-manifestation, preferred term, adverse effect onset date, adverse effect stop date, outcome, age, gender, product, and causality.

Reconciliation application 102 may execute an ETL operation to extract the data corresponding to the one or more columns in the second set of columns. Furthermore, reconciliation application 102 may execute an ETL operation to transform the extracted data such that it can be loaded into data repository 124, as described above.

Reconciliation application 102 may execute an ETL operation to load the transformed data into data repository 124. The transformed data may be loaded into the respective columns in data repository 124.

Reconciliation application 102 may correlate each row of data corresponding to first database 118 in data repository 124 to a respective row of data corresponding to second database 122 based on an identifier value stored in each row of data corresponding to first database 118 and each row of data corresponding to second database 122. For example, each row of data corresponding to first database 118 in data repository 124 may include a site number, subject ID, and AER number. Furthermore, each row of data corresponding to second database 122 in data repository 124 may also include a site number, subject ID, and AER number. As such, reconciliation application 102 may match one or more of the site number, subject ID, and AER number from a row corresponding to first database 118 in data repository 124 to a respective row corresponding to second database 120 in data repository 124.

Reconciliation application 102 may compare the data values in each row corresponding to first database 118 in data repository 124 to a correlated row corresponding to second database 122 in data repository 124. Reconciliation application 102 may identify differences in the data values based on the comparison. The differences may include a mismatch of data or missing data values. The mismatch in data may indicate that first database 118 and second database 120 have a different data value in an entry corresponding to a common column and row. The missing data value may indicate that either first database 118 or second database 124 is missing a data value.

Reconciliation application 102 may generate an output indicating the identified differences. Reconciliation application 102 may also generate visual indicators to highlight the identified differences. The visual indicators may be different based on the type of difference. The type of differences may include but are not limited to: missing data value in first database 118, missing data value in second database 122, and mismatch in a particular column.

The output may be safety reconciliation report 200. Safety reconciliation report 200 may be a spreadsheet that includes columns in data repository 124, the data values for the respective rows corresponding to first database 118 and second database 122. Safety reconciliation report 200 may be output as a file to application 112. Alternatively, safety reconciliation report 200 may be displayed on a user interface on application 112.

In some embodiments, reconciliation application 102 may automatically execute an action in first database 118 or second database 120 to resolve an identified difference. For example, in the event reconciliation application 102 identifies a missing data value in first database 118 that is present in second database 120, reconciliation application 102 may store the data value, as indicated in second database 120, in first database 118. Similarly, in the event reconciliation application 102 identifies a missing data value in second database 120 that is present in first database 118, reconciliation application 102 may store the data value, as it is indicated in first database 118, in second database 120.

Furthermore, in the event reconciliation application 102 identifies a mismatch in data values in first database 118 and second database 120, reconciliation application 102 may determine which data value is likely to be the accurate data value. For example, reconciliation application 102 may determine that the accuracy of the other data values in the row, including the data value and corresponding to first database 118, is more than a predetermined threshold. Furthermore, reconciliation application 102 may determine that the accuracy of the other data values in the row, including the data value and corresponding to second database 122, is less than the predetermined threshold. As a result, reconciliation application 102 may determine that the data value in first database 118 is likely accurate. Consequently, reconciliation application 102 may update the data value in second database 122 to match the data value in first database 118.

In some embodiments, reconciliation application 102 may use the following logic for extracting seriousness and outcome data from one or more data files received from clinical sub-system 114-1:

Scenario 1

The one or more data files may include multiple rows for a case for a continuous event for the case (e.g., multiple events of a headache for the same case). Both events are labeled as serious. In this scenario, reconciliation application 102 may extract an outcome (e.g., recovered/resolved) from the latest record and the earliest adverse effect onset date of the two events.

Scenario 2

The one or more data files may include multiple rows for a case for a continuous event for the case (e.g., multiple events of a headache for the same case). The first event is labeled as serious, and the second event is not labeled as serious. In this scenario, reconciliation application 102 may extract an outcome (e.g., recovered/resolved) from the latest record and the earliest adverse effect onset date of the two events.

Scenario 3

The one or more data files may include multiple rows for a case for a continuous event for the case (e.g., multiple events of a headache for the same case) and a different event (e.g., nausea) for the same case. Reconciliation application 102 may extract the data for the continuous event and the different event. Reconciliation application 102 extract the earliest adverse effect onset date of the continuous event.

Scenario 4

The one or more data files may include multiple rows for a case for a continuous event for the case (e.g., multiple events of a headache for the same case) and a different event (e.g., nausea) for the same case. The continuous event and the different event are not labeled as serious. Reconciliation application 102 may not process these events for safety gateway reconciliation report 200.

FIG. 3 is a graphical user interface part of an output generated by the system for reconciling data stored in disparate data storage devices, according to some embodiments. As indicated with respect to FIG. 2, the output may be safety reconciliation report 200. The output may be a graphical user interface (GUI) displayed on application 112 executing on client device 110. Alternatively, the output may be a GUI displayed on an internet browser on client device 110. In another example, the output may be a file (e.g., PDF, spreadsheet, DOC, TXT, CSV, etc.) transmitted to client device 110.

The output may include GUI 300. GUI 300 may provide a summary of the output. Specifically, GUI 300 may provide a summary of the safety reconciliation report. The summary may include a protocol number. The protocol number may be an identifier of a clinical trial. The safety reconciliation report may correspond to the particular clinical trial corresponding to the protocol number.

The summary may further include a number of cases identified in the clinical database (e.g., first database 118 as shown in FIG. 1), the number of cases identified in the safety database (e.g., second database 122 as shown in FIG. 2), the total number of events identified in the clinical database, and the total number of events identified in the safety database.

The summary may further indicate that the safety reconciliation report identifies any cases that are missing in the safety database, any cases that are missing in the clinical database, and any mismatches in data values between the safety and clinical databases.

FIG. 4 is a graphical user interface part of an output generated by the system for reconciling data stored in disparate data storage devices, according to some embodiments. As indicated above, the output may be a safety reconciliation report. The safety reconciliation report may include GUI 400. GUI 400 may be rendered after GUI 300 of FIG. 3.

GUI 400 may be a spreadsheet that indicates the identified differences between the clinical database (e.g., first database 118, as shown in FIG. 1) and safety database (e.g., second database 122, as shown in FIG. 1). GUI 400 may include columns 420 from a data repository (e.g., data repository 124 as shown in FIG. 1). Columns 420 may have corresponding columns in the clinical database and the safety database. Furthermore, columns 420 may be related to clinical trials and safety reports related to drugs and products. As a non-limiting example, columns 420 may include source, site number, subject ID, AER number, case ID, reported term, seriousness, co-manifestation, preferred term, adverse effect onset date, adverse effect stop date, outcome, age, gender, product, casualty, and mismatch. Columns 420 may store data related to a drug, product, subject, and a reported adverse effect on the subject associated with the drug or product.

The source column may include data values indicating whether the row corresponds with the clinical or safety database. The mismatch column may include data values indicating whether there is a mismatch between the data values.

The rows of the spreadsheet in GUI 400 may be from the data repository. However, each row may correspond with the clinical or safety database. The source column may indicate whether the row corresponds with the clinical or safety database.

The spreadsheet in GUI 400 may include a legend 401 and may include a protocol ID 402. Legend 401 may indicate the types of identified differences between the clinical trial and safety databases and the corresponding visual indicator. The visual indicator may be different colors, patterns, haptic effects, animation, shapes, etc. As a non-limiting example, legend 401 may indicate the following types of identified differences: missing in the clinical database, missing in the safety database, event/case attribute mismatch, and casualty mismatch. Although not shown in legend 401, preferred term mismatch may also be a type of difference. The event/case attribute mismatch may be a mismatch corresponding to any of the data values corresponding to the following columns: seriousness, adverse effect stop date, outcome, age, or gender. Legend 401 may also indicate that if there is no identified difference, there may be an absence of a visual indicator (e.g., a blank or white background).

The spreadsheet in GUI 400 may be ordered such that the correlated rows corresponding to the safety and clinical databases are grouped. As a non-limiting example, the row corresponding to clinical data is rendered before the correlated row corresponding to safety data. In addition, the visual indicators indicating the differences in the data values may be rendered on or with respect to the respective data values.

As a non-limiting example, row 403 may correspond to the clinical database, and row 404 may correspond to the safety database. Row 403 and 404 may be correlated with each other. For example, rows 403 and 404 may be associated with the same subject, case, and AER number. GUI 400 may indicate an identified mismatch with respect to the data values for rows 403 and 404 under the seriousness column. Row 403 may indicate a data value of "Yes" under the seriousness column, and row 404 may indicate a data value of "No" under the seriousness column. A visual indicator may be rendered on the data values for rows 403 and 404 under the seriousness column. The visual indicator may correspond with the visual indicator for an event/case attribute mismatch as indicated in legend 401.

GUI 400 may also indicate a mismatch with respect to the data values for rows 403 and 404 under the causality column. For example, row 403 may indicate a data value of "Not Suspected" under the causality column, and row 404 may indicate a blank data value under the causality column. Therefore, a visual indicator may be rendered on the data values for rows 403 and 404 under the causality column. The visual indicator may correspond with the visual indicator for causality mismatch, as indicated in legend 401.

Continuing with the non-limiting example, row 406 may correspond with the clinical database, and row 408 may correspond to the safety database. Row 406 and 408 may be correlated with each other. For example, rows 406 and 408 may be associated with the same subject, case, and AER number. GUI 400 may indicate that data values for row 408 are missing in the safety database. A visual indicator may be rendered on the entirety of row 408. The visual indicator may correspond with the visual indicator for missing in the safety database, as indicated in legend 401.

Continuing with the non-limiting example, row 410 may correspond with the clinical database, and row 412 may correspond to the safety database. Row 410 and 412 may be correlated with each other. Rows 410 and 412 may be associated with the same subject, case, and AER number. GUI 400 may indicate that data values for row 410 are missing in the clinical database. A visual indicator may be rendered on the entirety of row 412. The visual indicator may correspond with the visual indicator for missing in the clinical database, as indicated in legend 401.

Continuing with the non-limiting example, row 414 may correspond to the clinical database, and row 416 may correspond to the safety database. Rows 414 and 416 may be correlated with each other. For example, rows 414 and 416 may be associated with the same subject, case, and AER number. GUI 400 may indicate an identified mismatch with respect to the data values for rows 414 and 416 under the outcome column. For example, row 414 may indicate a blank data value under the outcome column, and row 416 may indicate a data value of "Recovered" under the outcome column. A visual indicator may be rendered on the data values for rows 414 and 416 under the outcome column. The visual indicator may correspond with the visual indicator for an event/case attribute mismatch as indicated in legend 401.

GUI 400 may also indicate a mismatch with respect to the data values for rows 414 and 416 under the causality column. Row 414 may indicate a data value of "Suspected" under the causality column, and row 416 may indicate a blank data value under the causality column. A visual indicator may be rendered on the data values for rows 414 and 416 under the causality column. The visual indicator may correspond with the visual indicator for causality mismatch, as indicated in legend 401.

The spreadsheet may include several pages. A user may filter the spreadsheet of GUI 400 based on column type, difference type, data value (e.g., case ID), source (e.g., clinical or safety database), etc. Furthermore, a user may export the data into a commonly accepted formats of EXCEL, DOC, PDF, etc. Moreover, the user may export only filtered or selected data into a commonly accepted format. As a non-limiting example, the user may export instances of missing values in the clinical database into a commonly accepted format.

The output may also include a summary of the queries executed in the clinical database, the safety database, and the data repository to generate the output.

As a non-limiting example, the visual indicators for GUI 400 may be generated as follows for the following scenarios:
Scenario 1—Product Mismatch.

In the event there is an identified mismatch in the data values for the product column for correlated rows, GUI 400 will include a row for each combination of product and reported term for both the clinical and safety databases. The reported term column, co-manifestation column, adverse effect onset date column, and product column may be indicated as missing data values for the respective clinical and safety databases. For example, a first row corresponding to the clinical database may include a data value of product A under the product column. A second row, corresponding to the safety database and correlated to the first row, may include the data value of product B under the product column. In this scenario, GUI 400 will include a row corresponding with the clinical database with the data value of product A under the product column and the correlated row corresponding with the safety database. The correlated row corresponding to the safety database may indicate missing data values for the reported term column, co-manifestation column, adverse effect onset date column. Additionally, GUI 400 will include a row corresponding with the safety database with the data value of product B under the product column and the correlated row corresponding with the clinical database. The correlated row corresponding to the clinical database may indicate missing data values for the reported term column, co-manifestation column, adverse effect onset date column.

Scenario 2—Multiple Product and Event Combination in Safety and Clinical with Product Mismatch.

Two correlated rows may include data values for multiple events (e.g., multiple reported terms) and multiple products. The events may be the same; however, the products may be different. In this scenario, GUI 400 may include a row for each combination of product and reported term for both the clinical and safety databases.

For example, the data values for the product column in a first row, which corresponds to the clinical database, may include product A and the data values for the product column in a second row, which corresponds with the safety database, may include product B and C. Furthermore, the data values for the reported term column for the first row may include fever and cold. Similarly, the data values for the reported term column for the second row may also include fever and cold. In this scenario, GUI 400 may include a row corresponding to the clinical database, including the data value, product A, for the product column, and fever for the reported term column. The correlated row corresponding to the safety database may indicate missing data values for the reported term column, co-manifestation column, adverse effect onset date column, and product column. Additionally, GUI 400 may include a row corresponding to the clinical database, including the data value product A for the product column and cold for the reported term column. The correlated row corresponding to the safety database may indicate missing data values for the reported term column, co-manifestation column, adverse effect onset date column, and product column.

Furthermore, GUI 400 may include a row corresponding to the safety database, including the data value product B for product and fever for the reported term column. As a result, the correlated row corresponding to the clinical database may indicate missing data values for the reported term column, co-manifestation column, adverse effect onset date column, and product column. Moreover, GUI 400 may include a row corresponding to the safety database, including the data value product B for the product column and cold for the reported term column. The correlated row corresponding to the clinical database may indicate missing data values for the reported term column, co-manifestation column, adverse effect onset date column, and product column.

GUI 400 may also include a row corresponding to the safety database, including the data value product C for product and fever for the reported term column. The correlated row corresponding to the clinical database may indicate missing data values for the reported term column, co-manifestation column, adverse effect onset date column, and product column. Moreover, GUI 400 may include a row corresponding to the safety database, including the data value product C for product and cold for the reported term column. The correlated row corresponding to the clinical database may indicate missing data values for the reported term column, co-manifestation column, adverse effect onset date column, and product column.

Scenario 3—Blinded Product

A row corresponding to the clinical database may include the string "masked for" before the product name in the product column when the product is blinded in the clinical trial. The string "masked for" may be removed when comparing the data value for the product column with the data value for the product column in the correlated row corresponding to the safety database.

Scenario 4—Co-Manifestations Mapped in the Safety Database

A row corresponding to the safety database may include multiple data values for reported terms and multiple data values for the co-manifestation column. For example, the row may include progression of cancer and cancer as data values for the reported term column and "N" for progression of cancer, and "Y" for cancer under the co-manifestation column. The row corresponding to the clinical database may include progression of cancer as the data value for the reported term column and "N" for the data value under the co-manifestation column.

GUI 400 may include two correlated rows corresponding to the clinical and safety databases, for which the data value under the reported term column is progression of cancer and the data value for co-manifestation is "N." Furthermore, GUI 400 may include a row corresponding to the safety database, for which the data value under the reported term column is cancer and the data value for co-manifestation is "Y." The correlated row corresponding to the clinical database may indicate missing data values for the reported term column, co-manifestation column, adverse effect onset date column, and product column.

Scenario 5—Causality

If there is any mismatch between the data values under causality in rows corresponding to the clinical and safety databases, GUI 400 may indicate a mismatch between the data values. This is true even when there is a blank data value under causality for rows corresponding to either the clinical or safety databases.

Scenario 6—Multiple Episodes of an Event with Different Adverse Effect Onset Dates A row corresponding to the safety or clinical database may indicate multiple events under the reported term column and multiple adverse effect onset dates. For example, a first row corresponding to the clinical database may indicate headache under the reported term column, Jun. 8, 2019 under the adverse effect onset date, and Jun. 22, 2019 under the adverse effect stop date. A second row corresponding to the safety database may indicate two events of headache under the reported term column, Jun. 8, 2019 under the adverse effect onset date for the first headache event, Jun. 20, 2019 under the adverse effect onset date for the second headache event, Jun. 14, 2019 under the adverse effect stop date for the first headache event, and Jun. 22, 2019 under the adverse effect stop date for the second headache event.

In this scenario, GUI 400 may include a row corresponding to the clinical database for which the data values for the reported term column is a headache, the data value for the adverse effect onset date column is Jun. 8, 2019, and the adverse effect stop date column is Jun. 22, 2019. Furthermore, GUI 400 may include a row corresponding to the safety database for which the data values for the reported term column is headache (e.g., first headache event), the data value for the adverse effect onset date column is Jun. 8, 2019, and the adverse effect stop date column is Jun. 14, 2019. GUI 400 may visually indicate a mismatch for the data values for the adverse effect stop date column.

Furthermore, GUI 400 may include a row corresponding to the safety database for which the data values for the reported term is headache (e.g., second headache event), the data value for the adverse effect onset date column is Jun. 20, 2019, and the adverse effect stop date is Jun. 22, 2019. In addition, the correlated row corresponding to the clinical database may indicate missing data values for the reported term column, co-manifestation column, adverse effect onset date column, and product column.

Scenario 7—Multiple Episodes of an Event with Different Adverse Effect Onset Dates Rows corresponding to the clinical or safety databases may include imprecise or partial dates for adverse effect onset date column and adverse effect stop date column. In this scenario, GUI 400 may visually indicate a mismatch for the data values under the adverse effect onset date column.

Scenario 8—Adverse Effect Onset Date Mismatch

Rows corresponding to the clinical or safety databases may include different adverse effects on set dates. As a result, these may be treated as separate adverse events. For example, a first row corresponding to the clinical database may include Jun. 7, 2019 for the adverse effect onset date column, and a second row corresponding to the safety database may include Jun. 8, 2019 for the adverse effect onset date column. In this scenario, GUI 400 may include a row corresponding to the safety database, indicating Jun. 8, 2019 for the adverse effect onset date column. In addition, the correlated row corresponding to the clinical database may indicate missing data values for the reported term column, co-manifestation column, adverse effect onset date column, and product column.

Additionally, GUI 400 may include a row corresponding to the clinical database, indicating Jun. 7, 2019 for the adverse effect onset date column. The correlated row corresponding to the safety database may indicate missing data values for the reported term column, co-manifestation column, adverse effect onset date column, and product column.

Figure 5:
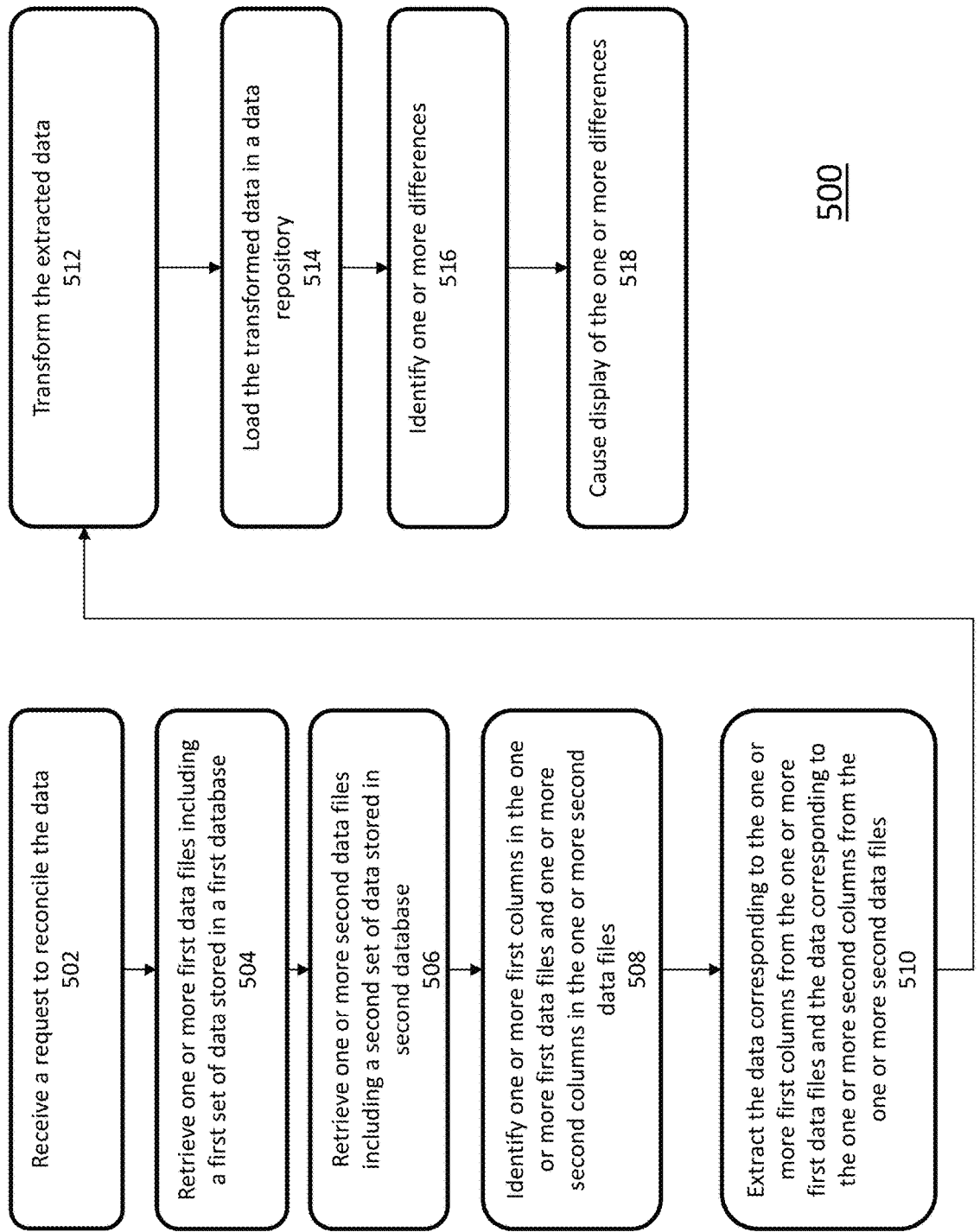
FIG. 5 is a flowchart illustrating a process for identifying differences in data stored in disparate databases, according to some embodiments.

FIG. 5 is a flowchart illustrating a process for identifying differences in data stored in disparate databases, according to some embodiments. Method 500 can be performed by processing logic that can comprise hardware (e.g., circuitry, dedicated logic, programmable logic, microcode, etc.), software (e.g., instructions executing on a processing device), or a combination thereof. It is to be appreciated that not all steps can be needed to perform the disclosure provided herein. Further, some of the steps can be performed simultaneously or in a different order than shown in FIG. 5, as will be understood by a person of ordinary skill in the art.

Method 500 shall be described with reference to FIG. 1. However, method 500 is not limited to that example embodiment.

In 502, reconciliation application 102 of server 100 receives a request to reconcile the data stored in first database 118 and second database 120 from application 112 of client device 110. The request may include an identifier of first database 118 and second database 120. As an example, first database 118 may store clinical trial data, and second database 122 may store safety data associated with a drug or product. As such, the request may also include an identifier of a clinical trial, product, and/or drug. Therefore, reconciliation application 102 may identify first database 118 and second database 122 using the identifier of one or more of first database 118, second database 120, clinical trial, product, or drug.

In 504, reconciliation application 102 retrieves one or more first data files including a first set of data stored in first database 118. Reconciliation application 102 may interface with API 120 to access the one or more data files. API 120 may expose the one or more data files to reconciliation application 102. The one or more data files may be spreadsheets. The one or more data files may include the columns of first database 118.

In 506, reconciliation application 102 retrieves one or more second data files, including a second set of data stored in second database 122. The one or more second data files may include the columns of second database 122.

In 508, reconciliation application 102 identifies one or more first columns in the one or more first data files and one or more second columns in the one or more second data files. Reconciliation application 102 identifies the one or more first and second columns corresponding to the data is to be loaded in data repository 124.

In 510, reconciliation application 102 extracts the data corresponding to the one or more first columns from the one or more first data files and the data corresponding to the one or more second columns from the one or more second data files. Reconciliation application 102 may perform an ETL operation to extract the data.

In 512, reconciliation application 102 transforms the data extracted from the one or more first data files and the one or more second data files. Reconciliation application 102 may perform an ETL operation to transform the data. In addition, reconciliation application 102 may transform the extracted data such that the extracted data is compatible with and can be loaded in data repository 124.

In 514, reconciliation application 102 loads the transformed data extracted from the one or more first data files and the one or more second data files in data repository 124. Reconciliation application 102 may perform an ETL operation to load the data. The transformed data may be loaded into the respective columns of data repository 124. The columns of data repository 124 may correspond to the one or more first columns and the one or more second columns.

In 516, reconciliation application 102 identifies one or more differences between the data extracted from the one or more first data files and the data extracted from the one or more second data files in the data repository. The differences may be a mismatch of data values or a missing data value.

In 518, reconciliation application 102 causes display of the one or more differences. The output may include visual indicators identifying the differences. The visual indicators may be different based on the type of difference. The visual indicators may include but are not limited to: highlighting in different colors, animation, patterns, haptic outputs, gradients, shapes, or visual effects.

Figure 6:
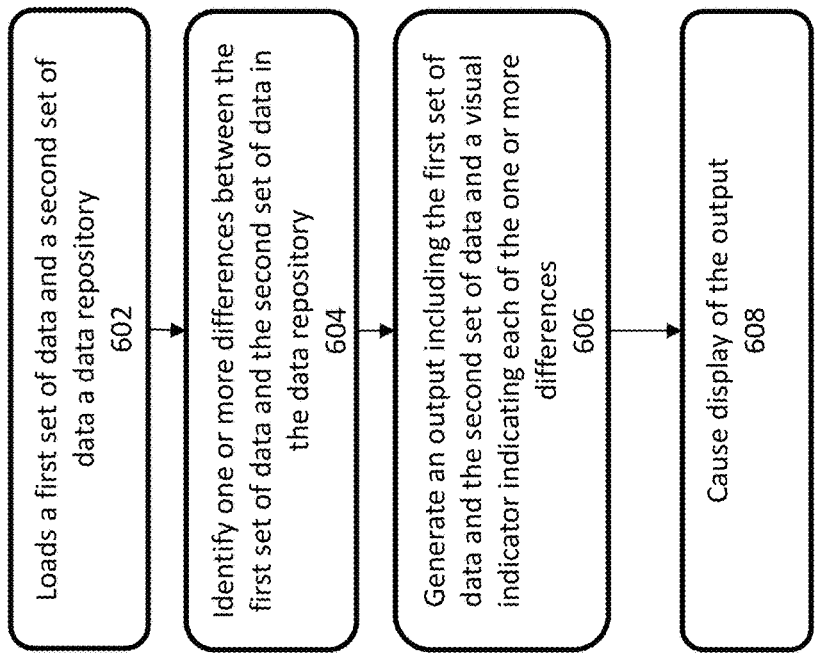
FIG. 6 is a flowchart illustrating a process for generating and outputting an output indicating the differences between data in disparate data storage devices, according to some embodiments.

FIG. 6 is a flowchart illustrating a process for generating and outputting an output indicating the differences between data in disparate data storage devices, according to some embodiments. Method 600 can be performed by processing logic that can comprise hardware (e.g., circuitry, dedicated logic, programmable logic, microcode, etc.), software (e.g., instructions executing on a processing device), or a combination thereof. It is to be appreciated that not all steps can be needed to perform the disclosure provided herein. Further, some of the steps can be performed simultaneously or in a different order than shown in FIG. 6, as will be understood by a person of ordinary skill in the art.

Method 600 shall be described with reference to FIGS. 1-2. However, method 600 is not limited to that example embodiment.

In 602, reconciliation application 102 loads a first set of data corresponding to one or more first columns of a first database and a second set of data corresponding to one or more second columns of a second database into a data repository. The first set of data includes one or more first rows, and the second set of data includes one or more second rows. The data repository includes a set of columns corresponding to the first and second sets of data.

In 604, reconciliation application 102 identifies one or more differences between the first set of data and the second set of data in the data repository. The differences may be a mismatch of data values between the first set of data and the second set of data. Alternatively, the differences may be a missing data value in the first set of data or the second set of data.

In 606, reconciliation application 102 generates an output including the first set of data and the second set of data and a visual indicator indicating each of the one or more differences. The output may be one or more graphical user interfaces (GUI) to be rendered on client device 110. Furthermore, output may be a file, such as a spreadsheet. The visual indicator may be different based on the type of difference. For example, the type of difference may be a mismatch or missing value.

In 608, reconciliation application 102 causes display of the output on a user interface of application 112. The output may be a file (e.g., spreadsheet) that is transmitted to client device 110.

Figure 7:
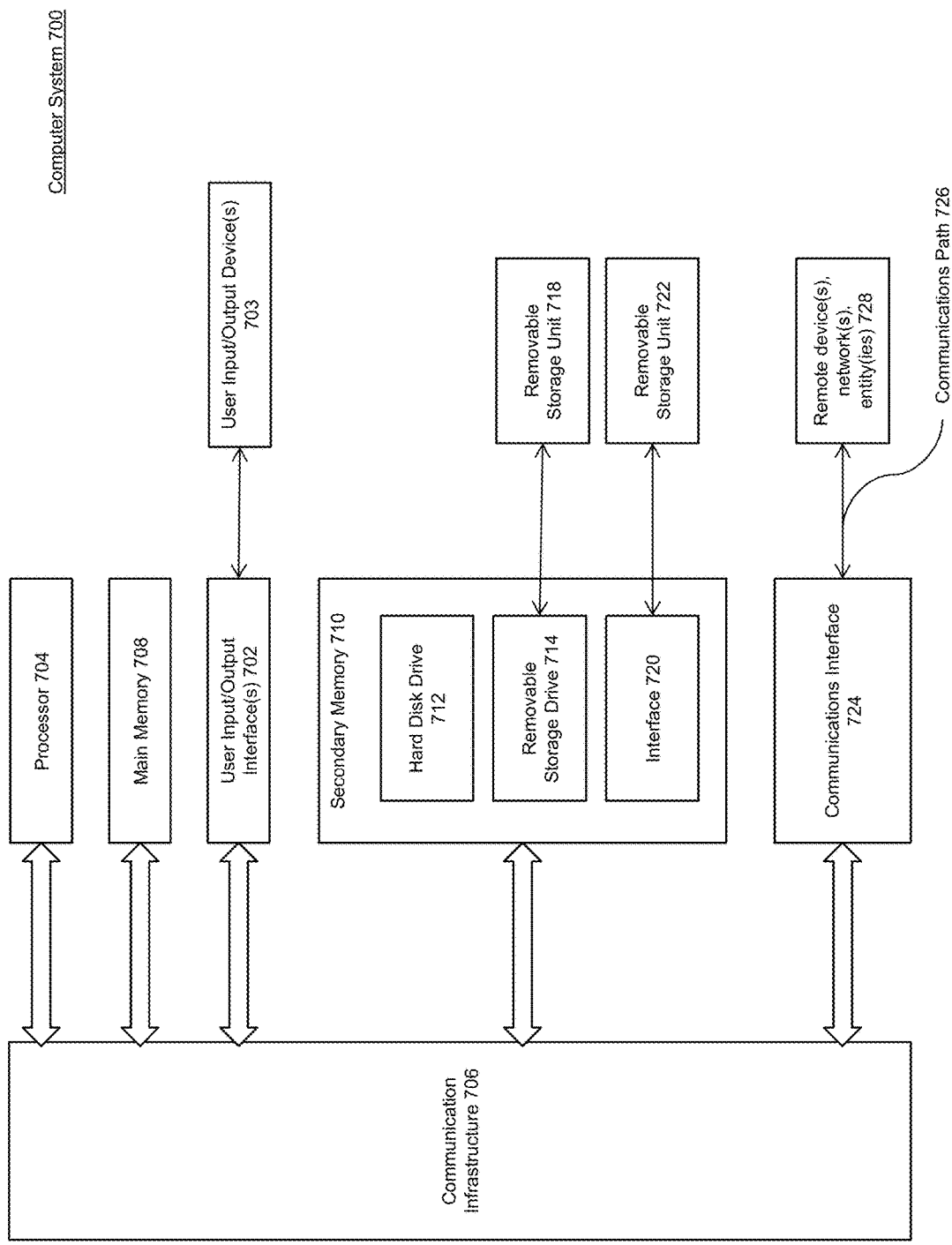
FIG. 7 is a block diagram of example components of a device according to some embodiments.

Various embodiments can be implemented, for example, using one or more computer systems, such as computer system 700 shown in FIG. 7. Computer system 700 can be used, for example, to implement methods 500 of FIG. 5 and 600 of FIG. 6. Furthermore, computer system 700 can be at least part of server 100, client device 110, first sub-system 114, second sub-system 116, first database 118, second database 120, and data repository 124, as shown in FIG. 1. For example, computer system 700 route communication to various applications. Computer system 700 can be any computer capable of performing the functions described herein.

Computer system 700 can be any well-known computer capable of performing the functions described herein.

Computer system 700 includes one or more processors (also called central processing units, or CPUs), such as a processor 704. Processor 704 is connected to a communication infrastructure or bus 706.

One or more processors 704 can each be a graphics processing unit (GPU). In some embodiments, a GPU is a processor that is a specialized electronic circuit designed to process mathematically intensive applications. The GPU can have a parallel structure that is efficient for parallel processing of large blocks of data, such as mathematically intensive data common to computer graphics applications, images, videos, etc.

Computer system 700 also includes user input/output device(s) 703, such as monitors, keyboards, pointing devices, etc., that communicate with communication infrastructure 706 through user input/output interface(s) 702.

Computer system 700 also includes a main or primary memory 708, such as random access memory (RAM). Main memory 708 can include one or more levels of cache. Main memory 708 has stored therein control logic (i.e., computer software) and/or data.

Computer system 700 can also include one or more secondary storage devices or memory 710. Secondary memory 710 can include, for example, a hard disk drive 712 and/or a removable storage device or drive 714. Removable storage drive 714 can be a floppy disk drive, a magnetic tape drive, a compact disk drive, an optical storage device, tape backup device, and/or any other storage device/drive.

Removable storage drive 714 can interact with a removable storage unit 718. Removable storage unit 718 includes a computer usable or readable storage device having stored thereon computer software (control logic) and/or data. Removable storage unit 718 can be a floppy disk, magnetic tape, compact disk, DVD, optical storage disk, and/any other computer data storage device. Removable storage drive 714 reads from and/or writes to removable storage unit 718 in a well-known manner.

According to an exemplary embodiment, secondary memory 710 can include other means, instrumentalities, or other approaches for allowing computer programs and/or other instructions and/or data to be accessed by computer system 700. Such means, instrumentalities, or other approaches can include, for example, a removable storage unit 722 and an interface 720. Examples of the removable storage unit 722 and the interface 720 can include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 700 can further include a communication or network interface 724. Communication interface 724 enables computer system 700 to communicate and interact with any combination of remote devices, remote networks, remote entities, etc. (individually and collectively referenced by reference number 728). For example, communication interface 724 can allow computer system 700 to communicate with remote devices 728 over communications path 726, which can be wired and/or wireless, and which can include any combination of LANs, WANS, the Internet, etc. Control logic and/or data can be transmitted to and from computer system 700 via communication path 726.

In some embodiments, a tangible, non-transitory apparatus or article of manufacture comprising a tangible, non-transitory computer useable or readable medium having control logic (software) stored thereon is also referred to herein as a computer program product or program storage device. This includes, but is not limited to, computer system 700, main memory 708, secondary memory 710, and removable storage units 718 and 722, as well as tangible articles of manufacture embodying any combination of the foregoing. Such control logic, when executed by one or more data processing devices (such as computer system 700), causes such data processing devices to operate as described herein.

Based on the teachings contained in this disclosure, it will be apparent to persons skilled in the relevant art(s) how to make and use embodiments of this disclosure using data processing devices, computer systems, and/or computer architectures other than that shown in FIG. 7. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc., using orderings different than those described herein.

References herein to "one embodiment," "an embodiment," "an example embodiment," or similar phrases indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other but yet still co-operate or interact with each other.

The breadth and scope of this disclosure should not be limited by any of the above-described exemplary embodiments but should be defined only in accordance with the following claims and their equivalents.

What is claimed is:

1. A method for reconciling data stored in disparate data storage devices, the method comprising:
retrieving, by a processor, one or more first data files including a first set of data stored in a first database;
retrieving, by the processor, one or more second data files including a second set of data stored in a second database;
identifying, by the processor, one or more first columns in the one or more first data files and one or more second columns in the one or more second data files;
loading, by the processor, a first subset of the first set of data and a second subset of the second set of data into a data repository, wherein the first subset of data corresponds to the one or more first columns and comprises one or more first rows each comprising a respective first data value and the second subset of data corresponds to the one or more second columns and comprises one or more second rows each comprising a respective second data value, and the data repository includes a set of third columns corresponding to the first subset of data and the second subset of data;
identifying, by the processor, a difference between a respective one of the first data values in a respective one of the one or more first rows of the first subset of data and a respective one of the second data values in a respective one of the one or more second rows of the second subset of data in the data repository;
based on identifying the difference, determining, by the processor, that the respective one of the first data values in the respective one of the one or more first rows have an accuracy level that satisfies a threshold amount;
updating, by the processor, the respective one of the second data values in the respective one of the one or more second rows in the second database to match the respective one of the first data values in the respective one of the one or more first rows in the first database based on determining that the accuracy level of the respective first data values in the respective one of the one or more first rows satisfies the threshold amount; and
causing display, by the processor, of the difference.

2. The method of claim 1, wherein identifying the difference between the respective one of the first data values and the respective one of the second data values comprises:
correlating, by the processor, each first row of the one or more first rows to a respective second row of the one or more second rows based on a comparison of a first identifier value stored in each first row of the one or more first rows and a second identifier value stored in each second row of the one or more second rows; and
matching, by the processor, the respective first data value stored in each first row of the one or more first rows to the respective second data value stored in a correlated second row of the one or more second rows.

3. The method of claim 2, wherein the first identifier value is a combination of two or more data elements stored in each respective first row of the one or more first rows and the second identifier value is a combination of two or more data elements stored in each respective second row of the one or more second rows.

4. The method of claim 1, wherein the difference includes a mismatch or missing data value.

5. The method of claim 1, further comprising generating, by the processor, a visual indicator for the difference, wherein a type of the visual indicator corresponds to a type of difference.

6. The method of claim 1, wherein retrieving the one or more first data files comprises interfacing, by the processor, with an Application Program Interface (API) of a type corresponding to a type of the first set of data.

7. The method of claim 1, wherein the first set of data includes clinical trial data and the second set of data includes safety data.

8. The method of claim 1, further comprising executing, by the processor, an action in the first database or the second database to resolve the difference.

9. The method of claim 1, wherein the difference comprises a mismatch between the respective one of the first data values in the respective one of the one or more first rows and the respective one of the second data values in the respective one of the one or more second rows, and wherein the respective one of the first data values and the respective one of the second data values correspond to a same third column of the set of third columns.

10. The method of claim 9,
wherein determining, by the processor, that the respective one of the first data values in the respective one of the one or more first rows have the accuracy level satisfying the threshold amount is based on determining that the difference comprises the mismatch between the respective one of the first data values and the respective one of the second data values.

11. The method of claim 9, further comprising
determining, by the processor, that the respective one of the second data values is incorrect based on determining that the accuracy level of the respective one of the first data values in the respective one of the one or more first rows satisfies the threshold amount.

12. The method of claim 1, wherein the first set of data and second set of data includes one or more common data values associated with pharmacovigilance (PV).

13. A system for reconciling data stored in disparate data storage devices, the system comprising:
a memory; and
a processor coupled to the memory, the processor is configured to:
retrieve one or more first data files including a first set of data stored in a first database;
retrieve one or more second data files including a second set of data stored in a second database;
identify one or more first columns in the one or more first data files and one or more second columns in the one or more second data files;
load a first subset of the first set of data and a second subset of the second set of data into a data repository, wherein the first subset of data corresponds to the one or more first columns and comprises one or more first rows each comprising a respective first data value and the second subset of data corresponds to the one or more second columns and comprises one or more second rows each comprising a respective second data value, and the data repository includes a set of third columns corresponding to the first subset of data and the second subset of data;
identify a difference between a respective one of the first data values in a respective one of the one or more first rows of the first subset of data and a respective one of the second data values in a respective one of the one or more second rows of the second subset of data in the data repository;
based on identifying the difference, determine that the respective one of the first data values in the respective one of the one or more first rows have an accuracy level that satisfies a threshold amount;

update the respective one of the second data values in the respective one of the one or more second rows in the second database to match the respective one of the first data values in the respective one of the one or more first rows in the first database based on determining that the accuracy level of the respective first data values in the respective one of the one or more first rows satisfies the threshold amount; and cause display of the difference.

14. The system of claim 13, wherein identifying the difference between the respective one of the first data values and the respective one of the second data values comprises:

correlating, by the processor, each first row of the one or more first rows to a respective second row of the one or more second rows based on a comparison of a first identifier value stored in each first row of the one or more first rows and a second identifier value stored in each second row of the one or more second rows; and matching, by the processor, the respective first data value stored in each first row of the one or more first rows to the respective second data value stored in a correlated second row of the one or more second rows.

15. The system of claim 14, wherein the first identifier value is a combination of two or more data elements stored in each respective first row of the one or more first rows and the second identifier value is a combination of two or more data elements stored in each respective second row of the one or more second rows.

16. The system of claim 13, wherein the difference includes a mismatch or missing data value.

17. The system of claim 13, wherein the processor is configured to generate a visual indicator for the difference, wherein a type of the visual indicator corresponds to a type of difference.

18. The system of claim 13, wherein retrieving the one or more first data files comprises interfacing with an Application Program Interface (API) of a type corresponding to a type of the first set of data.

19. The system of claim 13, wherein the first set of data includes clinical trial data and the second set of data includes safety data.

20. The system of claim 13, wherein the processor is further configured to execute an action in the first database or the second database to resolve the difference.

21. The system of claim 13, wherein the difference comprises a mismatch between the respective one of the first data values in the respective one of the one or more first rows and the respective one of the second data values in the respective one of the one or more second rows, and wherein the respective one of the first data values and the respective one of the second data values correspond to a same third column of the set of third columns.

22. The system of claim 21, wherein determining that the respective one of the first data values in the respective one of the one or more first rows have the accuracy level satisfying the threshold amount is based on determining that the difference comprises the mismatch between the respective one of the first data values and the respective one of the second data values.

23. The system of claim 21, wherein the processor is further configured to determine that the respective one of the second data values is incorrect based on determining that the accuracy level of the respective one of the first data values in the respective one of the one or more first rows satisfies the threshold amount.

24. A non-transitory computer-readable medium having instructions stored thereon, execution of which, by one or more processors of a device, cause the one or more processors to perform operations comprising:

retrieving one or more first data files including a first set of data stored in a first database;

retrieving one or more second data files including a second set of data stored in a second database;

identifying one or more first columns in the one or more first data files and one or more second columns in the one or more second data files;

loading a first subset of the first set of data and a second subset of the second set of data into a data repository, wherein the first subset of data corresponds to the one or more first columns and comprises one or more first rows each comprising a respective first data value and the second subset of data corresponds to the one or more second columns and comprises one or more second rows each comprising a respective second data value, and the data repository includes a set of third columns corresponding to the first subset of data and the second subset of data;

identifying a difference between a respective one of the first data values in a respective one of the one or more first rows of the first subset of data and a respective one of the second data values in a respective one of the one or more second rows of the second subset of data in the data repository;

determining that the respective one of the first data values in the respective one of the one or more first rows have an accuracy level that satisfies a threshold amount;

updating the respective one of the second data values in the respective one of the one or more second rows in the second database to match the respective one of the first data values in the respective one of the one or more first rows in the first database based on determining that the accuracy level of the respective first data values in the respective one of the one or more first rows satisfy the threshold amount; and causing display of the one or more differences.

\* \* \* \* \*